(12) United States Patent
Stehle et al.

(10) Patent No.: US 11,744,553 B2
(45) Date of Patent: Sep. 5, 2023

(54) ULTRASOUND SYSTEM, METHOD AND COMPUTER PROGRAM PRODUCT

(71) Applicant: KONINKLIJKE PHILIPS N.V., Eindhoven (NL)

(72) Inventors: Thomas Heiko Stehle, Hamburg (DE); Frank Michael Weber, Hamburg (DE); Christian Buerger, Hamburg (DE); Irina Waechter-Stehle, Hamburg (DE); Jörg Sabczynski, Norderstedt (DE); Michael Grass, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 614 days.

(21) Appl. No.: 16/336,496

(22) PCT Filed: Sep. 29, 2017

(86) PCT No.: PCT/EP2017/074835
§ 371 (c)(1),
(2) Date: Mar. 26, 2019

(87) PCT Pub. No.: WO2018/060456
PCT Pub. Date: Apr. 5, 2018

(65) Prior Publication Data
US 2021/0282748 A1 Sep. 16, 2021

(30) Foreign Application Priority Data
Sep. 29, 2016 (EP) ..................................... 16191398

(51) Int. Cl.
*A61B 8/00* (2006.01)
*A61B 8/08* (2006.01)
(Continued)

(52) U.S. Cl.
CPC .......... *A61B 8/4494* (2013.01); *A61B 8/0825* (2013.01); *A61B 8/4209* (2013.01);
(Continued)

(58) Field of Classification Search
CPC ... A61B 8/4494; A61B 8/4254; A61B 8/0825; A61B 8/4209; G01S 15/8952; G01S 15/8934; G01S 7/52079
See application file for complete search history.

(56) References Cited

U.S. PATENT DOCUMENTS

| | | | |
|---|---|---|---|
| 5,735,282 | A | 4/1998 | Hossack |
| 5,997,479 | A | 12/1999 | Savord et al. |

(Continued)

FOREIGN PATENT DOCUMENTS

| | | | |
|---|---|---|---|
| JP | 2002301074 | A | 10/2002 |
| JP | 2009247511 | A | 10/2009 |

(Continued)

OTHER PUBLICATIONS

English machine-generated translation of Sakamoto et al. (JP 2002-301074) (Year: 2021).*

(Continued)

*Primary Examiner* — Christopher Koharski
*Assistant Examiner* — Taylor Deutsch

(57) ABSTRACT

An ultrasound system is disclosed comprising an ultrasound transducer array (100) comprising a plurality of ultrasound transducer cells (130), each of said cell having an independently adjustable position and/or orientation such as to conform an ultrasound transmitting surface of the cell to a region of a body and a controller (140). The controller is configured to register the respective ultrasound transducer cells by simultaneously operating at least two ultrasound transducer cells in a transmit mode in which the cells transmit distinguishable ultrasound signals and operating the (Continued)

remaining ultrasound transducer cells in a receive mode. The controller extracts time-of-flight information of the respective ultrasound signals between transmitter and receiver and by systematically selecting different ultrasound transducer cells as transmitters, the controller collects sufficient time-of-flight information from which the respective position and/or relative orientation of the ultrasound transducer cells within the ultrasound transducer array may be derived. A method for operating the ultrasound system in this manner as well as a computer program product is also disclosed.

19 Claims, 10 Drawing Sheets

(51) Int. Cl.
*G01S 15/89* (2006.01)
*G01S 7/52* (2006.01)

(52) U.S. Cl.
CPC ........ *A61B 8/4254* (2013.01); *G01S 15/8934* (2013.01); *G01S 15/8952* (2013.01); *G01S 7/52079* (2013.01)

(56) References Cited

U.S. PATENT DOCUMENTS

| | | | |
|---|---|---|---|
| 6,013,032 A | 1/2000 | Savord | |
| 6,120,453 A | 9/2000 | Sharp | |
| 6,157,592 A | 12/2000 | Kriz et al. | |
| 6,283,919 B1 | 9/2001 | Roundhill et al. | |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 7,497,828 B1 | 3/2009 | Wilk et al. | |
| 2002/0188198 A1 | 12/2002 | Hong | |
| 2005/0020921 A1 | 1/2005 | Glassell et al. | |
| 2013/0242705 A1* | 9/2013 | Kim | H04R 31/00 367/181 |
| 2014/0058263 A1 | 2/2014 | Baym et al. | |
| 2014/0163375 A1* | 6/2014 | Wasielewski | A61B 8/4227 600/443 |
| 2015/0257733 A1 | 9/2015 | Corbett, III et al. | |
| 2017/0103540 A1* | 4/2017 | Brokman | A61B 6/5247 |

FOREIGN PATENT DOCUMENTS

| | | |
|---|---|---|
| WO | 32091927 A1 | 11/2002 |
| WO | 2016063163 A1 | 4/2016 |

OTHER PUBLICATIONS

Duck, F., "Physical Properties of Tissues: A Comprehensive Reference Book", Academic Press (1990) (Abstract).

* cited by examiner

ULTRASOUND SYSTEM, METHOD AND COMPUTER PROGRAM PRODUCT

This application is the U.S. National Phase application under 35 U.S.C. § 371 of International Application No. PCT/EP2017/074835, filed on Sep. 29, 2017, which claims the benefit of European Application Serial No. 16191398.3, filed Sep. 29, 2016. These applications are hereby incorporated by reference herein.

FIELD OF THE INVENTION

The present invention relates to an ultrasound system including an ultrasound transducer array comprising a plurality of ultrasound transducer cells, each of said cells having an independently adjustable orientation such as to conform an ultrasound transmitting surface of the cell to a region of a body and a controller for controlling such an ultrasound transducer array.

The present invention further relates to a method of operating such an ultrasound system.

The present invention still further relates to a computer program product for visualizing data acquired with such an ultrasound system.

BACKGROUND OF THE INVENTION

Ultrasound waves find several applications in medicine. One such application is ultrasound imaging, wherein ultrasound waves are emitted by an ultrasound device comprising an array of ultrasound transducers into the body of a patient and echoes of the ultrasound waves are collected by the ultrasound transducers or by dedicated ultrasound receivers and processed to generate an ultrasound image, e.g. a 1D, 2D or 3D ultrasound image. Another application is ultrasound therapy such as high intensity focused ultrasound (HIFU) therapy in which ultrasound beams are generated by an ultrasound device comprising ultrasound transducer element tiles and are focused on diseased tissue. The significant energy deposition at the focus creates local temperatures in the range of about 65° C. to 85° C., which destroys the diseased tissue by coagulative necrosis.

Such ultrasound systems typically comprise an ultrasound transducer array, e.g. as part of an ultrasound probe, for delivering ultrasound waves to a subject, e.g. to a patient being imaged or treated. Such an ultrasound transducer array typically comprises a plurality of ultrasound transducers such as piezoelectric transducer elements formed of materials such as lead zirconate titanate (PZT) or polyvinylidene-fluoride (PVDF) and capacitive micro-machined ultrasonic transducer (CMUT) elements in which a membrane including a first electrode over a cavity comprising a second electrode opposite the first electrode and separated therefrom by the cavity is used to generate the ultrasound waves (or receive the ultrasound waves in a receive mode) through application of an appropriate stimulus, e.g. an alternating current, to the first and second electrodes. Increasingly, several of such ultrasound transducer elements are combined on so-called tiles, e.g. chips of a semiconductor substrate in which the ultrasound transducer elements are located, which tiles may have dimensions of several centimetres squared ($cm^2$) in some applications. This allows for the ultrasound transducer arrays to cover larger areas of the subject's body to be imaged or treated. The ultrasound transducer elements of such tiles may be grouped together and operated in unison, such that the tile behaves as a composite ultrasound transducer element comprising multiple facets, i.e. ultrasound transducer cells combining to form the composite ultrasound transducer element, or alternatively may be operated independently.

The placement of such large area ultrasound transducer arrays on a region of a patient's body has several advantages over hand-held ultrasound transducer probes. Not only is it possible to image (or treat) a larger portion of a patient's body in a single event, it becomes more straightforward to monitor progress of an anomaly in a particular region of the patient's body over time. A well-known problem associated with hand-held ultrasound transducer probes is that different operators may operate the probe in different manners, for example by applying a different pressure to the region of the patient's body under investigation, thereby causing a different deformation of such a body region, which may make it difficult to compare ultrasound images acquired by different operators. This problem is particularly relevant to breast examinations, e.g. to monitor the development of tumours in the breast of a female patient as the breast tissue is particularly malleable and therefore easily deformed.

WO 02/091927 A1 discloses a wearable breast tissue examination device including a support element adapted to fit over at least a portion of the breast of the wearer. The support element has a shell, a measurement apparatus including at least two mutually opposed ultrasound transducer arrays disposed of at least a portion of the inner surface of the shell and at least one bladder element disposed in the shell that is configured to orient the wearer's breast properly for examination. This examination device operates in a tomography-style manner in which one of the ultrasound transducer array acts in a transmission mode and the opposing ultrasound transducer array listens to the transmissions. The transducer arrays have a well-defined orientation relative to each other in order to facilitate the generation of 3-D ultrasound images with the examination device. However, such orientation requirements may preclude the establishment of an acoustic coupling between the ultrasound transducer arrays and the breast of the patient, for example in a scenario where the shape of the breast makes it difficult for the breast to comply with the shape of the examination device.

U.S. Pat. No. 6,120,453 discloses two or more ultrasound transducer probes applied to a body in order to give information regarding the relative position of each by determining the time of transit of sound energy between each probe. Besides knowledge of the range from one probe to another, the orientation and bearing of one probe to the other is determined by calculating the relative direction by which sound energy arrives at a probe. By making the location of one of the probes be known through fixing it in space to a mechanical arm or similar mechanical device of knowable position, the absolute positions and orientations of both probes becomes known. However, the use of multiple probes may not always be possible or desirable, e.g. when performing non-invasive ultrasound imaging or treatment.

Recently, flexible ultrasound transducer arrays have entered the market, which may exhibit improved compliance with a contoured surface, e.g. a curved portion of a patient's body such as a female breast. For such arrays, only a small amount of coupling gel may be required to improve acoustic coupling as the desired conformal coupling is largely achieved by the flexibility of the transducer array. However, operation of such ultrasound transducer arrays is not without challenges. In such arrays, the ultrasound transducer tiles have several degrees of freedom, e.g. translational freedom in the X, Y, Z-plane as well as tip/tilt freedom. In order to achieve coherent beamforming in such scenarios, the actual orientation (relative positions) of each ultrasound transducer tile must be known to the beamforming circuitry of an ultrasound system deploying such an ultrasound transducer array, i.e. the images generated with the respective tiles must be spatially registered. This typically requires the inclusion of orientation sensors associated with individual tiles.

An example of such an arrangement is disclosed in WO 2016/063163 A1, which discloses a transducer device including a transducer array contoured on a substrate. The substrate is configured to flex in accordance with a surface. The transducer array includes elements for transmitting and/or receiving acoustic energy. A shape-sensing optical fibre is disposed within the array and configured to shape sense a position of the elements in the array. In this manner, the relative orientation (position) of the respective ultrasound transducer elements may be derived from the shape sensing information derived from the shape-sensing optical fibre, which relative orientation information may be utilized to calibrate the transducer device such that 3-D images may be generated with the transducer array.

SUMMARY OF THE INVENTION

The present invention seeks to provide an ultrasound system including an ultrasound transducer array comprising ultrasound transducer cells having individually adjustable positions in which the actual position of the ultrasound transducer array may be obtained without the need for additional position sensors.

The present invention further seeks to provide a method of operating such an ultrasound system.

The present invention further seeks to provide a computer program product to facilitate the operation of such an ultrasound system.

According to an aspect, there is provided an ultrasound system comprising an ultrasound transducer array comprising a plurality of ultrasound transducer cells, each of said cells having an independently adjustable position and/or orientation such as to conform an ultrasound transmitting surface of the cell to a region of a body; and a controller configured to, simultaneously, select a first ultrasound transducer cell and generate a first ultrasound signal with the first ultrasound transducer cell; select a second ultrasound transducer cell and generate a second ultrasound signal with the second ultrasound transducer cell, the second ultrasound signal being distinguishable from the first ultrasound signal; and operate the remaining ultrasound transducer cells in a reception mode and receive respective indications of the reception of at least one of the first ultrasound signal and the second ultrasound signal from at least some of the remaining ultrasound transducer cells; wherein the controller is further configured to derive, for each ultrasound cell receiving at least one of the first ultrasound signal and the second ultrasound signal, time-of-flight information of the first ultrasound signal from the first ultrasound transducer cell to the receiving ultrasound transducer cell and/or of the second ultrasound signal from the second ultrasound transducer cell to the receiving ultrasound transducer cell from the corresponding respective indication; repeat said selecting until a defined number of ultrasound transducer cells have generated at least one of the first ultrasound signal and the second ultrasound signal; and determine the relative positions and/or relative orientations of the ultrasound transducer cells from the derived time-of-flight information.

The present invention is based on the insight that when a flexible ultrasound transducer array is deployed on the (convex) curvature of the patient's body, ultrasound signals transmitted by one of the ultrasound transducer cells may be received by at least some of the remaining ultrasound transducer cells of the ultrasound transducer array, with the time of flight of such ultrasound signals being indicative of the distance between the transmitting and receiving ultrasound transducer cells. Consequently, by systematically engaging a defined number of ultrasound transducer cells as ultrasound signal transmitters, a set of distances between different ultrasound transducer elements may be obtained by virtue of the required time of flight information from which the relative position and/or orientation of the respective ultrasound transducer cells can be derived. An important additional insight is that this registration process may be deployed in a time-efficient manner by simultaneously enabling a plurality, i.e. at least two, ultrasound transducer elements as such transmitters, as long as the ultrasound signals generated by the respective ultrasound transducer elements selected as transmitters are distinguishable, thereby significantly reducing the duration of the registration process compared to an implementation in which only a single ultrasound transducer cell is deployed as such an ultrasound signal transmitter at any given time. In a particularly advantageous embodiment, the first ultrasound signal and the second ultrasound signal are distinguishable from each other by virtue of having different frequencies. In this embodiment, the controller may be configured to determine a time of arrival of the first ultrasound signal and/or the second ultrasound signal at a receiving ultrasound transducer cell from a power spectrum of the ultrasound signal received by said receiving ultrasound transducer cell. This allows for a straightforward determination of the time of flight of such a signal, as the point in time at which a significant power surge at a relevant frequency component of the power spectrum is detected may be used to determine the time of flight of the received ultrasound signal characterized by the relevant frequency component.

Any suitable number of ultrasound transducer cells of the ultrasound transducer array may be deployed by the controller as transmitters during the registration process. This defined number of ultrasound transducer cells may equal the total number of ultrasound transducer cells in the ultrasound transducer array although in alternative embodiments the defined number is smaller than this total number. In other embodiments, the defined number may be determined on the fly, i.e. the registration procedure may be terminated as soon as sufficient information has been gathered to reconstruct the surface carrying the ultrasound transducer cells.

In embodiments of the present invention, the ultrasound system is a diagnostic imaging system although alternatively or additionally the ultrasound system may be a therapy system such as a HIFU system.

In a particularly advantageous embodiment, the ultrasound system may be a wearable system, in which case the ultrasound system may be incorporated in a garment. Such a garment preferably is a brassiere comprising a pair of cups, at least one of said cups comprising the ultrasound transducer array. Embodiments of the present invention are particularly suited to diagnostic imaging and/or therapeutic treatment of (female) breasts, because the curvature of such breasts ensures that most if not all ultrasound transducer cells deployed in a brassiere can receive ultrasound signals transmitted by other cells in the ultrasound transducer array, which therefore makes the registration process using the aforementioned time of flight information particularly suitable in such application domains.

Each cup of the brassiere may comprise an independently operable ultrasound transducer array such that each breast may be independently monitored and/or treated. Alternatively, only one of the cups may comprise an ultrasound transducer array of the ultrasound system according to embodiments of the present invention, which for example may be a suitable embodiment in case only one of the breasts of the patient is to be monitored or treated with the ultrasound system.

Each cup of the brassiere comprising an ultrasound transducer array may further comprise a plurality of apertures for receiving biopsy needles. This for example is particularly advantageous if a biopsy is to be performed on a tissue area within the breast, in which case the ultrasound transducer array may assist in guiding the biopsy needle to the appropriate tissue area, with the apertures facilitating insertion of such a biopsy needle through the skin of the breast in the region proximal to the tissue area, thereby minimizing the distance the biopsy needle has to travel to reach the tissue area of interest.

Such an ultrasound system incorporated in a brassiere may further comprise at least one dispensing unit for dispensing an acoustic coupling gel between an ultrasound transducer array in one of said cups and a breast of a patient in order to assist in improving the conformal contact between an ultrasound transducer cell and the opposing portion of the breast in contact with the cell.

The ultrasound system may further comprise a transmission unit for transmitting data collected with the ultrasound transducer array to a remote device such as a mobile communication device. This for instance may be used to send diagnostic imaging information to the remote device such that the state of the part of the body of the patient under observation, e.g. a breast of a female patient, may be remotely assessed, e.g. by a medical practitioner. This obviates the need for the patient to frequently visit a clinic or the like, which therefore may be perceived as more convenient and less stressful by the patient. The transmission unit may be a wireless transmission unit in some embodiments.

In an embodiment, the controller is further configured to, for each ultrasound transducer cell, generate a further ultrasound signal with the ultrasound transducer cell; receive an echo signal of the further ultrasound signal from the ultrasound transducer cell; derive an acoustic coupling quality indication for the ultrasound transducer cell from a difference between the further ultrasound signal and its received echo signal; and transmit the acoustic coupling quality indication to a remote device with the transmission unit. Such acoustic coupling quality indication information may be used as the remote device to create a graphic representation or the like on a display of the remote device to inform the wearer of the ultrasound transducer array, e.g. a wearer of a brassiere in which the ultrasound transducer array is incorporated, if the ultrasound transducer array is correctly applied to the appropriate body part, and if not, to guide the wearer of the ultrasound transducer array to adjust the array accordingly, for example by indicating which parts of the ultrasound transducer array, i.e. which ultrasound transducer cells, have not formed a contact of sufficient quality with the part of the body to be imaged or treated.

In accordance with another aspect, there is provided a method of operating an ultrasound system comprising an ultrasound transducer array comprising a plurality of ultrasound transducer cells, each of said cell having an independently adjustable position and/or orientation such as to conform an ultrasound transmitting surface of the cell to a region of a body, the method comprising, simultaneously, selecting a first ultrasound transducer cell and generate a first ultrasound signal with the first ultrasound transducer cell; selecting a second ultrasound transducer cell and generate a second ultrasound signal with the second ultrasound transducer cell, the second ultrasound signal being distinguishable from the first ultrasound signal; and operating the remaining ultrasound transducer cells in a reception mode and receive respective indications of the reception of at least one of the first ultrasound signal and the second ultrasound signal from at least some of the remaining ultrasound transducer cells; the method further comprising deriving, for each ultrasound cell receiving at least one of the first ultrasound signal and the second ultrasound signal, time-of-flight information of the first ultrasound signal from the first ultrasound transducer cell to the receiving ultrasound transducer cell and/or of the second ultrasound signal from the second ultrasound transducer cell to the receiving ultrasound transducer cell from the corresponding respective indication; repeating said selecting until a defined number of ultrasound transducer cells have generated at least one of the first ultrasound signal and the second ultrasound signal; and determining the relative positions and/or orientations of the ultrasound transducer cells from the derived time-of-flight information.

As also explained above, such a registration method of the respective ultrasound transducer cells of the ultrasound transducer array allows for a straightforward registration of the respective cells without the need for additional sensors or the like, whilst the parallel transmission of at least two distinguishable ultrasound signals by different ultrasound transducer cells during the registration process furthermore ensures that such a registration method can be performed significantly more quickly compared to for example registration methods in which only one cell operates as such an ultrasound signal transducer at any given point in time during the registration process.

The method may further comprise, for each ultrasound transducer cell, generating a further ultrasound signal with the ultrasound transducer cell; receiving a signal echo of the further ultrasound signal from the ultrasound transducer cell; deriving an acoustic coupling quality indication for the ultrasound transducer cell from a difference between the further ultrasound signal and its received echo signal; and transmitting the acoustic coupling quality indication to a remote device. These indications for instance may be utilized by the remote device to visualize the quality of contact between the respective ultrasound transducer cells and the patient's body, such that the patient can adjust the ultrasound transducer array if necessary based on visual feedback information derived from the respective indications.

According to yet another aspect, there is provided a computer program product comprising a computer readable storage medium having computer readable program instructions embodied therewith for, when executed on a processor of a remote device, e.g. a mobile communication device, cause the processor to receive acoustic coupling quality indication information from the ultrasound system according to any of the above embodiments; and display the acoustic coupling quality indication information on a display of the remote device. Such a computer program product may be used to configure a mobile communication device such as a tablet computer or smart phone to assist a user of the ultrasound system according to embodiments of the present invention to correctly position the ultrasound transducer array of such an ultrasound system on the relevant part of the patient's body, e.g. the breast of a female patient.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
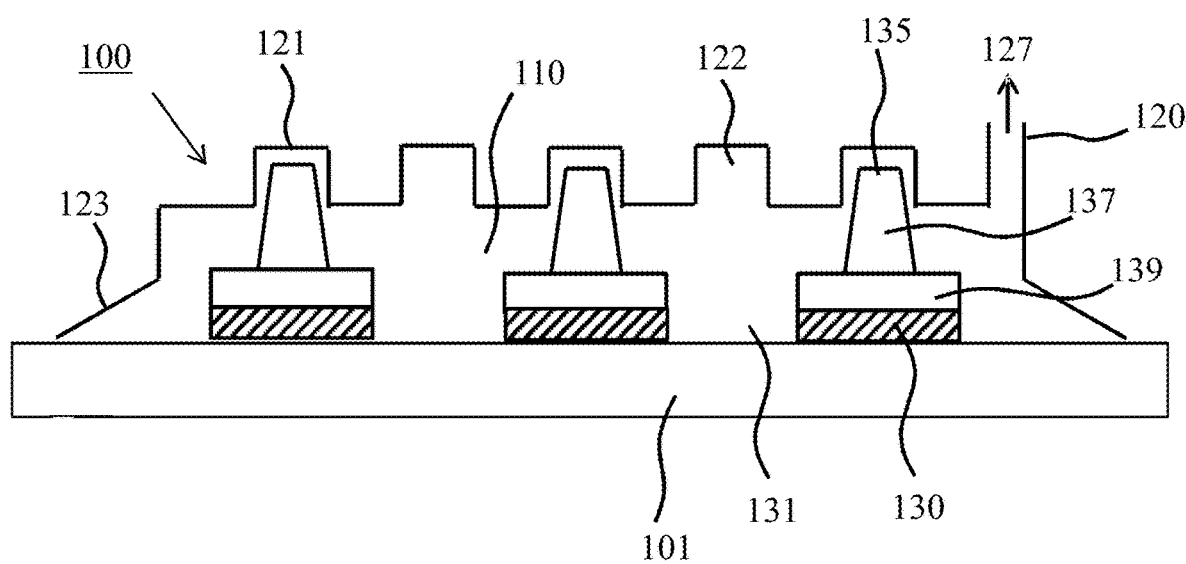
FIG. 1 schematically depicts an ultrasound transducer array of an ultrasound system according to an example embodiment.

It should be understood that the Figures are merely schematic and are not drawn to scale. It should also be understood that the same reference numerals are used throughout the Figures to indicate the same or similar parts.

FIG. 1 schematically depicts an ultrasound transducer array 100 of an ultrasound system according to an example embodiment. The ultrasound transducer array 100 may be designed for positioning on a region of a body of a patient for ultrasound imaging of a body portion of the patient, or alternatively or additionally, for therapeutic treatment of the body portion, e.g. in case of the ultrasound transducer array 100 forming part of a HIFU system. The ultrasound transducer array 100 comprises independently adjustable ultrasound transducer cells 130, which may be implemented as ultrasound transducer tiles. The ultrasound transducer cells 130 may be individual ultrasound transducer elements although in particularly advantageous embodiments each ultrasound transducer cell 130 comprises a plurality of ultrasound transducer elements, which for example may be arranged on an ultrasound transducer tile. Each tile may comprise one or more ultrasound transducer elements (not shown). Each tile for example may be a diced chip or the like onto which the one or more ultrasound transducer elements have been formed or mounted. In embodiments of the present invention, the ultrasound transducer elements may be implemented in any suitable manner. For example, the ultrasound transducer elements may be implemented by a piezoelectric ceramic material such as a lead zirconate titanate (PZT)-based material, a piezoelectric single crystal or composite material, a capacitive micromachined ultrasound transducer (CMUT) and so on. CMUT cells are specifically mentioned.

The ultrasound transducer cells 130 may have any suitable shape, e.g. a circular shape or polygonal shape. A polygonal shape such as a rectangular, e.g. square, shape, a hexagonal shape, and the like, is particularly mentioned as such a shape facilitates a close packing of the ultrasound transducer cells 130 within the transducer array, wherein the gap 131 between adjacent ultrasound transducer cells 130 is minimized. The avoidance of relatively large gaps 131 between adjacent ultrasound transducer cells 130 ensures that a substantially continuous image may be generated with the ultrasound transducer array 100 and may at least reduce the formation of ultrasound artifacts such as grating lobes.

The ultrasound transducer array 100 may have any suitable shape, e.g. may be a 1-dimensional or 2-dimensional ultrasound transducer array. In an embodiment, the ultrasound transducer array 100 comprises a plurality of ultrasound transducer tiles as the ultrasound transducer cells 130, each having a transducer surface area of several cm2, e.g. 2-50 cm2, to form a large area ultrasound transducer array 100. As will be explained in further detail below, in at least some embodiments, the ultrasound transducer array 100 is integrated in a garment such as a brassiere having a pair of cups for receiving female breasts in which each cup may comprise a separate ultrasound transducer array 100 integrated in the cup. Alternatively, only one of the cups of the brassiere may include such an ultrasound transducer array 100, e.g. a cup for receiving a breast in which anomalous tissue, e.g. cancerous tissue, has been detected.

Figure 2:
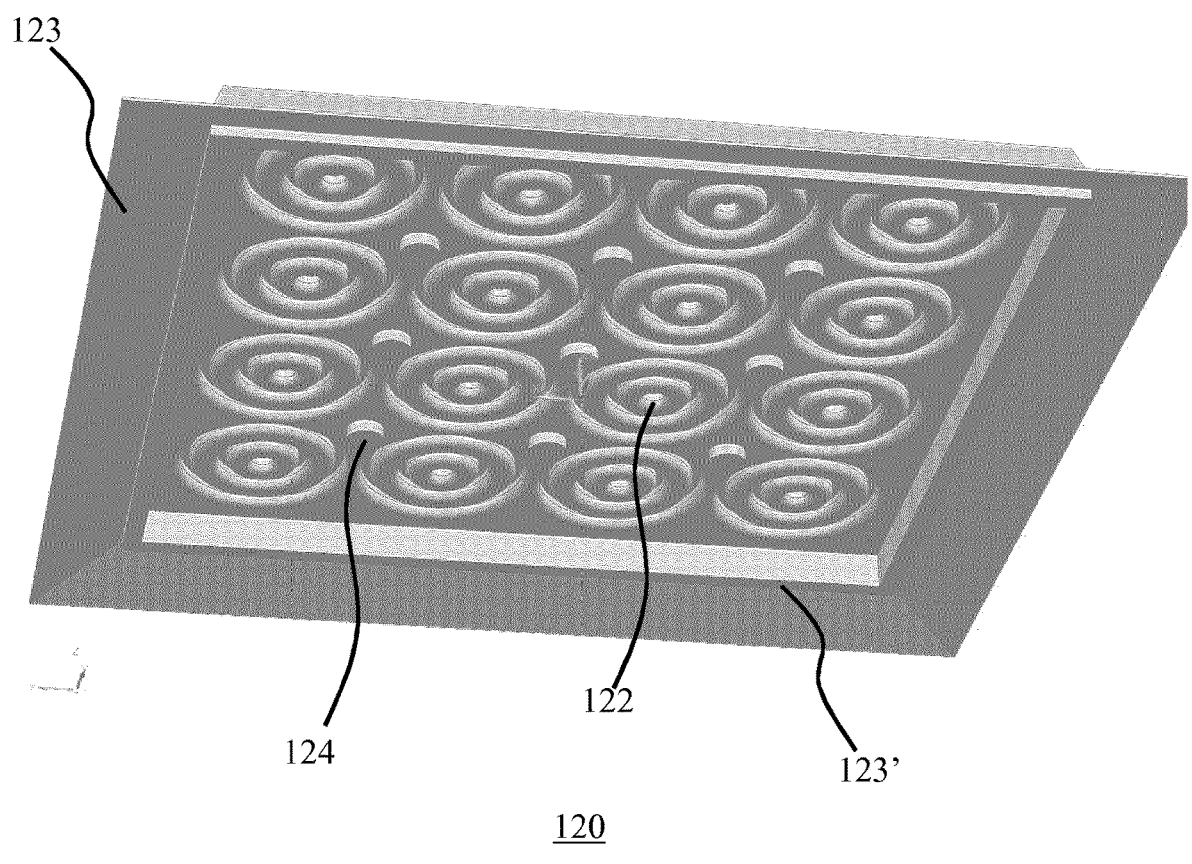
FIG. 2 schematically depicts an aspect of an ultrasound transducer array of an ultrasound system according to an example embodiment.

The ultrasound transducer array 100 may be adapted to transmit ultrasonic waves, e.g. ultrasound pulses, and receive (pulse) echo information as part of an ultrasound (diagnostic) imaging system to be described in more detail below. In case of a freestanding ultrasound transducer array 100, the array may comprise a body 120 having a mounting region 121 onto which the ultrasound transducer cells, e.g. tiles, 130 are mounted. A detail of such a body 120 is schematically depicted in FIG. 2. Although not shown, the transducer surfaces of the ultrasound transducer cells 130 may be covered by an acoustic layer, sometimes referred to as an acoustic window, in order to protect the ultrasound transducer array from being directly contactable, thereby protecting the transducer array from damage, as well as to protect the body of the subject, e.g. a patient, to be exposed to the ultrasound waves to be generated by the transducer array from being directly contacted by the transducer array, e.g. to protect the body from accidental electrical shock. As is well-known per se, such an acoustic window may further provide impedance matching between the transducer array and the body. The acoustic layer may be made of any material or combinations of materials known to the skilled person for such purposes.

The mounting region 121 of the body 120 may be flexible, which has the advantage that the mounting region 121 carrying the ultrasound transducer cells 130 may be deformed, e.g. to conform to a non-planar surface such as a contoured body of a patient to improve the quality of contact between the ultrasound transducer cells 130 and the patient's body. This is particularly relevant in case of large area ultrasound transducer arrays 100, where the array may need to conform to a large area of the patient's body, e.g. an area of several tens or hundreds of cm2. For example, the mounting region 121 may comprise an elastomer, i.e. a rubbery material, to provide the mounting region 121 with the desired flexibility. Examples of such an elastomer include a polyolefin, a diene polymer or a polysiloxane such as PDMS, a co-polymer or block-copolymer comprising a polyolefin, a diene polymer or a polysiloxane or a blend thereof although embodiments are not limited thereto. Polybutadiene, polydimethylsiloxane (PDMS) and relatively soft polyether block amides (PEBA) commonly used in catheters are specifically mentioned. A medical grade PDMS is particularly preferred. For example, the ultrasound transducer array 100 may be implemented as a flexible mat for conforming to the surface (i.e. skin of the body) of the subject.

Figure 3:
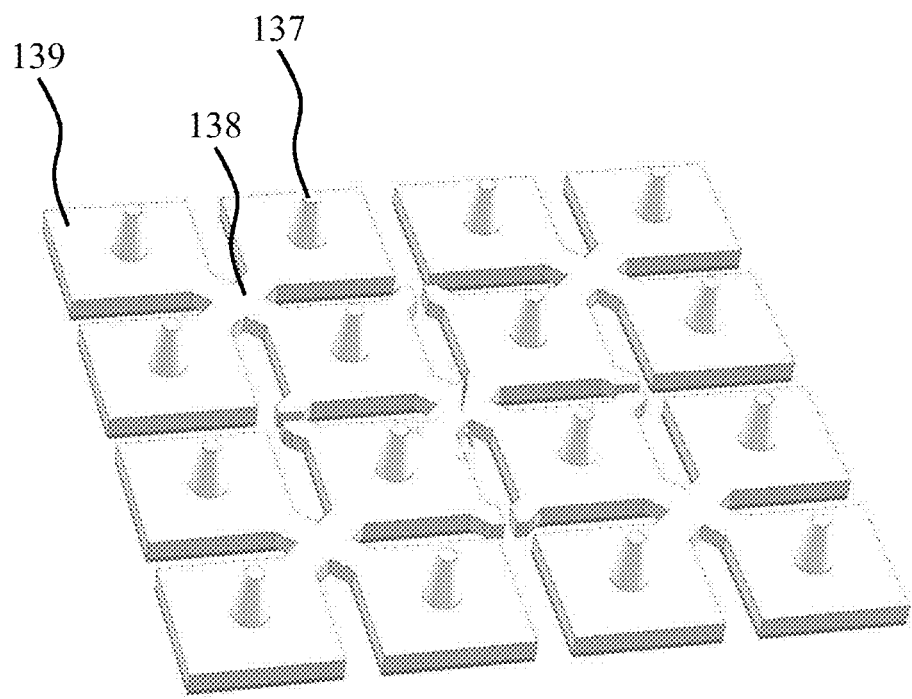
FIG. 3 schematically depicts another aspect of an ultrasound transducer array of an ultrasound system according to an example embodiment.
Figure 4:
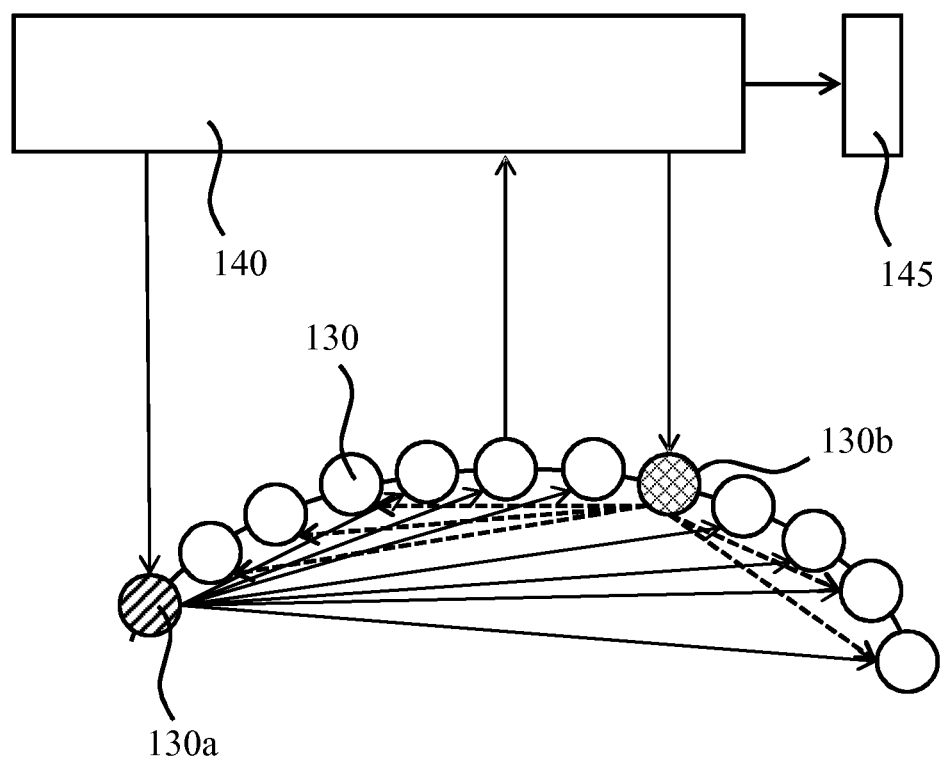
FIG. 4 schematically depicts an operating principle aspect of an ultrasound transducer array of an ultrasound system according to an example embodiment.

The ultrasound transducer cells 130 may be directly mounted onto the mounting region 121 in some embodiments (not shown). In alternative embodiments, such as the embodiment schematically depicted in FIG. 1, the mounting region 121 may comprise a plurality of receiving portions 122 for receiving a support member onto which ultrasound transducer cells 130 may be mounted. A detail of such a support member is schematically depicted in FIG. 3. The support members may each comprise a pillar 137 that fits into one of the receiving portions 122 of the mounting region 121. Each pillar 137 carries a mounting portion 139 onto which the ultrasound transducer cell 130 may be mounted. The support members may be made of a flexible material, e.g. a rubber-like material, and may be interconnected through mounting portions 139, e.g. to form a flexible mat 135 through interconnecting regions 138 in between adjacent mounting portions 139.

As shown in FIG. 3, each interconnecting region 138 connects four quadrants of mounting portions 139 that each have a corner interconnected to the interconnecting region 138. In this manner, each ultrasound transducer cell 130 will exhibit at least two degrees of rotational freedom, such that a good conformal contact with the body 101 of the subject can be achieved when the pressure in a space 110 is reduced by evacuation of a portion of air as explained in more detail below, with the resulting downward force on the mounting portions 139 as transferred through the pillars 137 being translated into the desired conformal contact of the ultrasound transducer cells 130 through these rotational degrees of freedom. In an alternative embodiment, the support member arrangement, e.g. mat 135 may be a rigid arrangement in which the mounting portions 139 are mounted on a flexible joint, e.g. a universal joint, a ball and socket joint, or the like.

The mounting region 121 may be delimited by a flexible lip 123 that is arranged to contact the subject upon placement of the ultrasound transducer array 100 on the subject. The lip 123 is flexible such that upon placement of the ultrasound transducer array 100 on the subject, the lip 123 seals the space 110 in between the mounting region 121 of the body 120 and the part of the subject's body 101 opposite the mounting region 121. The lip 123 may form an integral part of the body 120, or may be adhered or otherwise attached to the mounting region 121. The lip 123 may have any suitable shape that facilitates the formation of a sealed space 110 in between the ultrasound transducer cells 130 and the body of the subject upon placement of the ultrasound transducer array 100 on this body. The flexible lip 123 may be made of any suitable material, e.g. an elastomer as described above. In an embodiment, the mounting region 121 and the flexible lip 123 are made of the same material, with the flexible lip 123 preferably being integral to the mounting region 121, i.e. being formed from a single piece of flexible material. In an embodiment as depicted in FIG. 2, the lip 123 may include an edge 123' or may be separated from the space 110 by the edge 123', which edge 123' engages with the subject to reinforce the mounting region 121 in case of the pressure in the space 110 being reduced. The edge 123' may further assist in forming a seal between the ultrasound transducer array 100 and the subject such that an underpressure can be established in the space 110 as explained above.

The mounting region 121 of the body 120 may further comprise support portions 124 in between the receiving portions 122 that reinforce the mounting region 121 in case of the pressure in the space 110 being reduced. The mounting region 121 may be corrugated as schematically depicted in FIG. 1 such that the mounting region 121 can act as a spring. Consequently, when a volume of air is evacuated from the space 110 through outlet 127, e.g. using a vacuum pump or the like, to create an underpressure in the space 110, the atmospheric pressure over the ultrasound transducer array 100 forces the sprung mounting region 121 against the body 101. As little as a 10% reduction in pressure in the space 110 may suffice to achieve a downward pressure of 1N/cm2 on the mounting region 121.

It should be understood that the above described embodiments of the ultrasound transducer array 100 are by way of non-limiting examples only and that any ultrasound transducer array 100 comprising a plurality of ultrasound transducer cells, e.g. tiles, 130 that are independently adjustable such as to conform to a portion of the body of a patient may be used in the context of the present invention. In particular, in some embodiments the ultrasound transducer array 100 may be integrated into a garment such as a brassiere, in which case the respective ultrasound transducer cells 130 may be attached to a flexible material of the garment to give the ultrasound transducer cells 130 the desired degree of flexibility in order to conform to the shape of the body of the patient. Alternatively, any of the aforementioned embodiments of the ultrasound transducer array 100 may be included in such a garment.

As will be understood by the skilled person, in case of the ultrasound transducer array 100 conforming to a curved body portion, e.g. a female breast or the like, the various ultrasound transducer cells, e.g. tiles, 130 will assume different positions and/or orientations, i.e. positions or orientations in different planes, such that these positions and/or orientations need to be determined such that meaningful information, e.g. 3-D images, may be obtained from the ultrasound echoes received with the respective ultrasound transducer cells 130 in case of an ultrasound diagnostic imaging system or such that ultrasound beams may be focused on a common region within the body in case of an ultrasound therapy system such as a HIFU system. The determination of such position or orientation information is sometimes referred to as registration of the respective ultrasound transducer cells 130. As is well-known per se, the determination of such relative positions and/or orientations may be utilized by the ultrasound system such that ultrasound signals transmitted and/or received by the respective ultrasound transducer cells 130 may be referenced in accordance with a common reference frame, e.g. by transforming such signals in accordance with a position and/or orientation of a particular ultrasound transducer cell 130 relative to the common reference frame. In some embodiments, the ultrasound transducer cells 130 may be considered point sources of ultrasound radiation, in which embodiments the determination of the relative position of the ultrasound transducer cells 130 may suffice.

In accordance with an embodiment, the ultrasound system comprises a controller 140 for controlling the respective ultrasound transducer cells 130. Such a controller 140 may be implemented by one or more hardware components, e.g. integrated circuit components, an example embodiment of which will be described in more detail below. The controller 140 may be coupled to a communication unit 145 and adapted to control the communication unit 145 to transmit data obtained with the ultrasound transducer cells 130 to a remote device as will be explained in further detail below. The communication unit 145 may be a communication unit to be wired into a network connection, e.g. via an Ethernet port like, or alternatively may be a wireless communication unit. Any suitable wireless communication unit may be used for this purpose; by way of non-limiting example, the wireless communication unit may be a mobile communication unit adapted to communicate in accordance with a mobile communication standard such as GSM, UMTS or the like, a Wi-Fi communication unit, a Bluetooth communication unit, a NFC communication unit, and so on. The communication unit 145 in some embodiments may be adapted to communicate with a network interface, e.g. a modem, hub, router or the like, e.g. in the vicinity of the wireless communication unit, which network interface may relay the data received from the communication unit 145 to the remote device in any suitable fashion, e.g. over a wired or wireless network connection such as a LAN, WAN or the Internet. As such means of communication are well-known per se, this will not be explained in further detail for the sake of brevity only.

Figure 5:
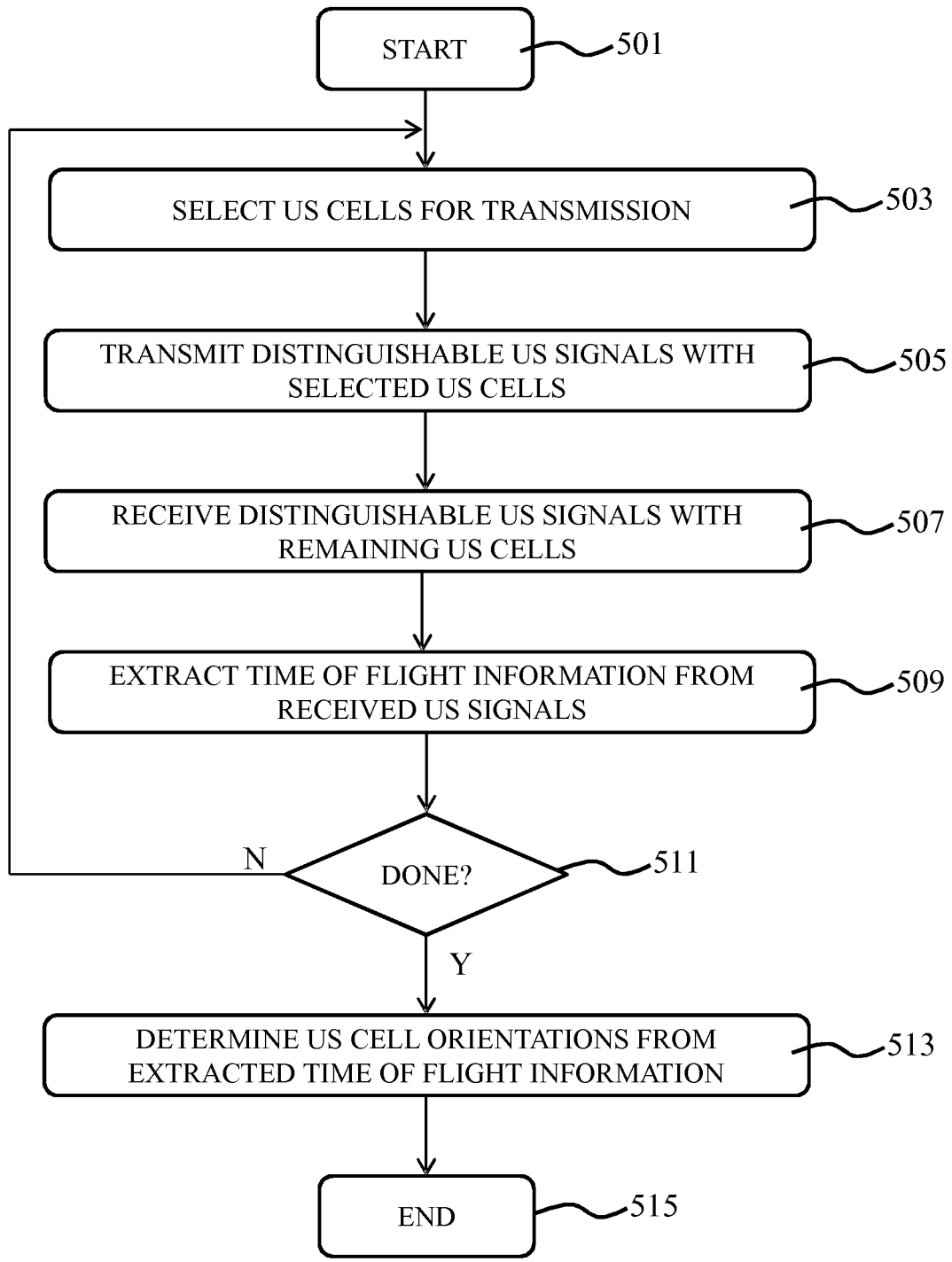
FIG. 5 is a flowchart of a method of operating an ultrasound system according to an embodiment.

The controller 140 may be adapted to perform a registration method in order to obtain the relative orientations of the respective ultrasound transducer cells 130. This method 500 will be explained in more detail with the aid of FIG. 5. The method 500 starts in 501, e.g. by activating the registration mode of the ultrasound system to which the controller 140 and the ultrasound transducer array 100 belongs. This may be achieved in any suitable manner, e.g. by a user activating the registration mode, e.g. after applying the ultrasound transducer array 100 to a body portion, which application may be realized by the user wearing a garment such as a brassiere including at least one such ultrasound transducer array 100. For example, the user may press a button or the like on the garment or on a separate user interface of the ultrasound system to indicate that the ultrasound transducer array 100 has been positioned on the part of the body to be imaged or treated. Alternatively, the registration mode may be automatically activated, for example upon the application of a power supply to the controller 140.

Next, the method 500 proceeds to 503 in which the controller 140 selects a first ultrasound transducer cell 130a and a second ultrasound transducer cell 130b for the simultaneous transmission of distinguishable ultrasound signals, i.e. ultrasound signals that may be distinguished from each other by receiving ultrasound transducer cells 130 of the ultrasound transducer array 100. In an embodiment, this is achieved by the controller 140 controlling the first ultrasound transducer cell 130a to transmit a first ultrasound signal having a first frequency and controlling the second ultrasound transducer cell 130b to transmit a second ultrasound signal having a second frequency different to the first frequency. The controller 140 at the same time switches the remaining ultrasound transducer cells 130 to a listening (receiving) mode in which the remaining ultrasound transducer cells 130 listen for the first and second ultrasound signals transmitted by the first and second ultrasound transducer cells 130a and 130b respectively.

The controller 140 subsequently causes the first ultrasound transducer cell 130a and the second ultrasound transducer cell 130b to simultaneously transmit the first and second ultrasound signals and registers the point in time T1 at which these signals are transmitted in 505. To this end, the controller 140 may include an internal clock or timer. Such internal clocks or timers are well-known per se and are therefore not described in further detail for the sake of brevity only; it suffices to state that any suitable implementation of such an internal clock or timer may be utilized.

In 507, the controller 140 receives indications from at least some of the respective ultrasound transducer cells 130 in listening mode that an ultrasound signal has been received, e.g. by virtue of the modulation of an electrical signal provided to the ultrasound transducer cell 130 as is well-known per se. The controller 140 may register the further point in time T2 corresponding to when the indication has been received and may evaluate the indication to determine which of the ultrasound signals, i.e. the first ultrasound signal or the second ultrasound signal, has been received by the ultrasound transducer cell 130. For example, in case of the first and second ultrasound signals having different frequencies, the controller 140 may evaluate the power spectrum of the signal received from the ultrasound transducer cell 130, e.g. by Fourier analysis, such that the arrival time T2 of a particular ultrasound signal may be derived from a sudden increase in power at the frequency of that particular ultrasound signal, such that the controller 140 may derive the time-of-flight $T_F$ of the particular ultrasound signal from its origin, i.e. the first ultrasound transducer cell 130a or the second ultrasound transducer cell 130b based on the difference between T2 and T1, i.e. $T_F$=T2−T1, in 509. As will be readily understood by the skilled person, the controller 140 may calculate $T_F$ for the respective ultrasound signals received by the ultrasound transducer cells 130 in listening mode at any suitable point in time, e.g. as soon as such a signal has been received, after all such signals have been received, after a defined period of time following the simultaneous transmission of the first and second ultrasound signals, which defined period of time may define the listening period of the remaining ultrasound transducer cells 130 or after all ultrasound transducer cells 130 to be operated in a transmission mode have transmitted their distinguishable ultrasound signals. Other suitable variants will be immediately apparent to the skilled person.

Next, the controller 140 checks in 511 if all target ultrasound transducer cells 130 of the ultrasound transducer array 100 have been operated in transmission mode. The number of target ultrasound transducer cells 130 may equal the total number of ultrasound transducer cells 130 in the ultrasound transducer array 100 or alternatively may be a number that is smaller than this total number but sufficient to obtain the necessary relative orientation information such that the respective ultrasound transducer cells 130 may be registered. If not every intended ultrasound transducer cell 130 has yet been operated in such a transmission mode, the method 500 reverts back to 503 in which the controller 140 selects the next two ultrasound transducer cells 130 of the ultrasound transducer array 100. This is repeated until all target ultrasound transducer cells 130 have been operated in the aforementioned transmission mode, after which the method 500 proceeds to 513 in which the relative positions and/or orientations of the respective ultrasound transducer cells 130 are determined by the controller 140 from the obtained time-of-flight information, after which the method 500 terminates in 515.

An example embodiment of how the position and/or orientation of the ultrasound transducer cells 130 is calculated from the time-of-flight information is now described in more detail in the following. From $T_F$ and the speed of sound in tissue, the distance D between a sender ultrasound transducer cell 130 and a receiver ultrasound transducer cell 130 can be calculated. With all the sender and receiver combinations that were measured, this gives a set of pairwise distances $D_{i,j}$ between different transducer cells i and j. Knowing that all elements are located on the same surface, e.g. a bra surface, the current shape of the surface can be reconstructed. To this end, an energy minimization formulism can, for example, be applied. In this formalism, an energy term is defined for each pairwise distance $D_{i,j}$ such that a spring connects the two points i and j, and the spring has its minimum energy at a length $D_{i,j}$. For estimating the surface shape, the points of the surface model are iteratively moved, and the current energy considering pairwise springs is re-evaluated. This is repeated until the energy converges to a minimum. An initial guess for the shape as a starting point for the optimization can be the average surface of the bra when applied to a patient. The orientation of the ultrasound transducer cells 130 can then be assumed to be normal to the surface at their specific locations. In this embodiment, each ultrasound transducer cell 130 may emit undirected (i.e. unfocused) pulses that are received by the other ultrasound transducer cells 130. In another embodiment in which the cell is capable to direct its pulses into certain directions, each ultrasound transducer cell 130 may emit several pulses in different directions, such that a receiving cell can detect which of the pulses it received with highest intensity. Then, information about the relative pairwise positioning and/or orientation between two transducer cells can be derived which can also be used for estimating or refining the global shape and/or orientation.

At this point, it is noted that the registration method 500 has been described in terms of simultaneously deploying two ultrasound transducer cells 130 in a transmission mode by way of non-limiting example only. It should be understood that the number of ultrasound transducer cells 130 simultaneously deployed in such a transmission mode may be increased to further decrease the duration of the registration method 500, as long as each ultrasound transducer cell 130 that is simultaneously deployed in such a transmission mode generates an ultrasound signal that, when received by another ultrasound transducer cell 130 in listening mode, can be distinguished from the other ultrasound signals generated at the same time as explained in more detail above.

Figure 6:
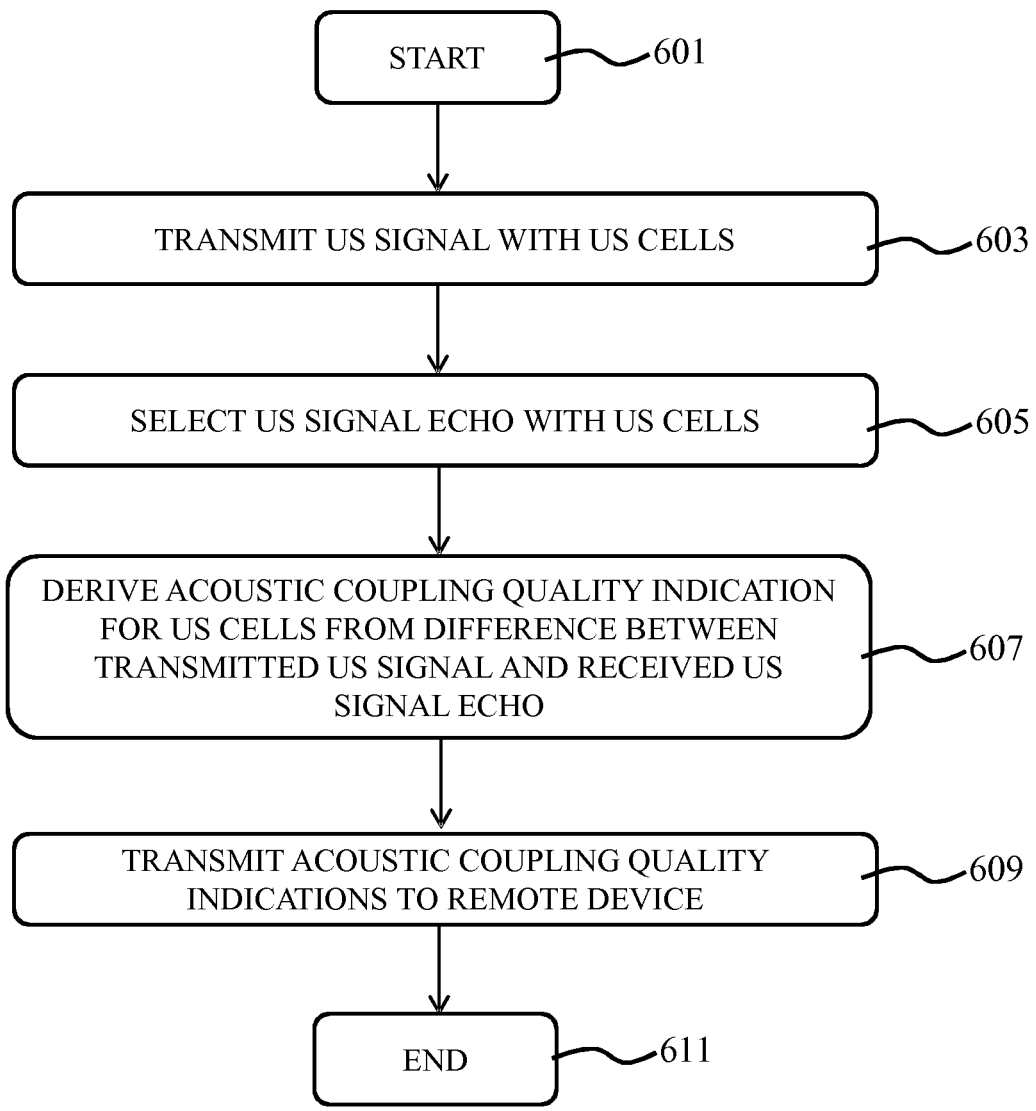
FIG. 6 is a flowchart of another method of operating an ultrasound system according to an embodiment.

The controller 140 may be further adapted to check if each ultrasound transducer cell 130, upon application of the ultrasound transducer array 100 to a body portion such as a female breast of the like, has achieved an acoustic coupling with that body portion of sufficient quality such that ultrasound pulses may be effectively delivered and/or received to this body portion with the ultrasound transducer cell 130. FIG. 6 is a flowchart of an example method 600 that may be deployed by the controller 140 for this purpose. The method 600 may commence in 601, e.g. by any suitable initiation of this verification process, after which the method 600 proceeds to 603 in which the controller 140 controls the ultrasound transducer cells 130 to transmit a reference ultrasound signal, e.g. a sequence or burst of ultrasound pulses, into the body portion. This may be done simultaneously or at least partially sequentially.

In 605, the controller 140 receives the pulse echoes of these reference ultrasound signals from the respective ultrasound transducer cells 130, after which the controller 140 in 607 derives an acoustic coupling quality indication from a difference between the transmitted reference ultrasound signal and its received echo. Such a difference for example may be determined based on at least one of a degradation of signal strength and signal shape.

Figure 7:
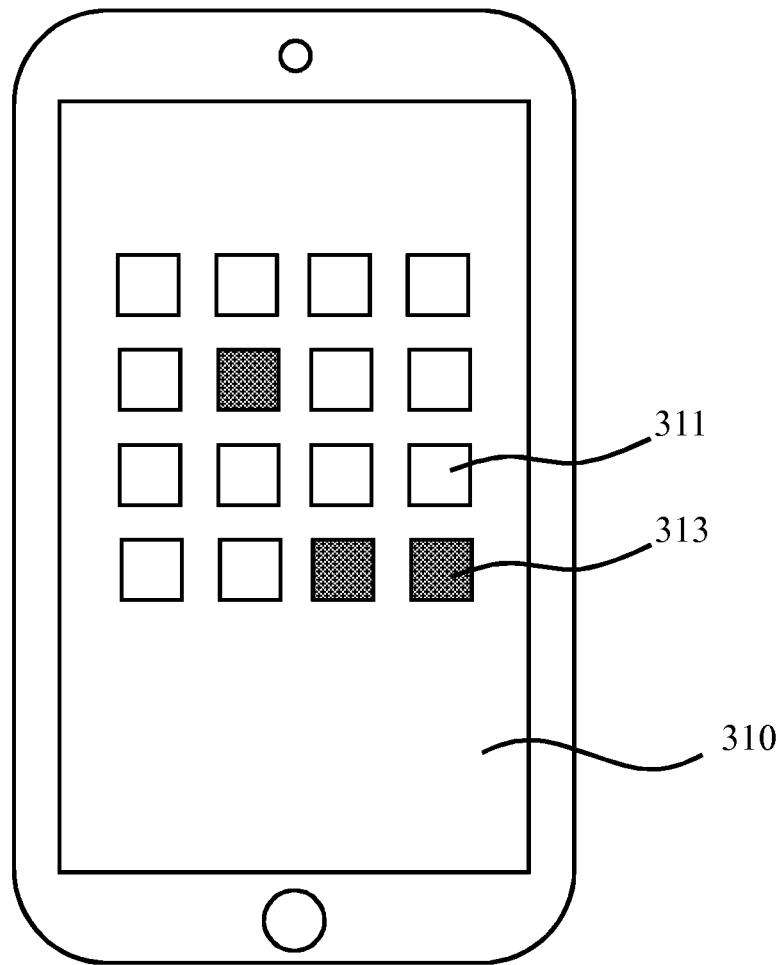
FIG. 7 schematically depicts a mobile communication device configured with a computer program product in accordance with an example embodiment.

In 609, the controller 140 may transmit the thus obtained acoustic coupling quality indications for the respective ultrasound transducer cells 130 to a remote device, for instance with the wireless communication unit 145, before the method 600 terminates in 611. The remote device may use the respective acoustic coupling quality indications as received from the controller 140 to visualize the quality of the acoustic coupling of the respective ultrasound transducer cells 130 to the body portion. For example, as schematically depicted in FIG. 7, the remote device may be a mobile communication device 300 such as a smart phone, tablet computer, or the like, having a display 310 under control of a processor (not shown), which processor may be coupled to a wireless communication unit (not shown) to receive the acoustic coupling quality indications from the wireless communication unit 145 and to convert these acoustic coupling quality indications into graphical representations 311, 313 of the ultrasound transducer cells 130 on the display 310 such that a user of the ultrasound transducer array 100 may determine based on the graphical representations 311, 313 which ultrasound transducer cells 130 are not properly acoustically coupled to the part of the body of the user to which the ultrasound transducer array 100 is applied, such that the user may learn from these graphical representations 311, 313 which part(s) of the ultrasound transducer array 100 need to be readjusted in order to achieve the desired acoustic coupling quality between the ultrasound transducer array 100 and the body portion.

For example, graphic representations 311 may indicate ultrasound transducer cells 130 having a good acoustic coupling with the body portion whilst graphic representations 313 may indicate ultrasound transducer cells 130 having insufficient acoustic coupling with the body portion. Any suitable graphical representations 311, 313 may be chosen for this purpose. By way of non-limiting example, graphical representations indicating a good acoustic coupling may be represented by a green colour whereas graphical representations indicating an insufficient acoustic coupling may be represented by a red colour but many other representations of course will be immediately apparent to the skilled person.

In order to configure the mobile communication device 300 such that the above visualization of the acoustic coupling quality is facilitated on the mobile communication device 300, a computer program product such as an app retrievable from an app store or the like may be made available. Such a computer program product may comprise a computer readable storage medium having computer readable program instructions embodied therewith for, when executed on the processor of a mobile communication device 300, cause the processor to receive the acoustic coupling quality indication information from the controller 140, e.g. by means of a wireless communication unit in the mobile communication device 300 as previously explained and display the acoustic coupling quality indication information on a display 310 of the mobile communication device, e.g. using graphical representations such as icons or the like as previously explained.

The controller 140 may be adapted to automatically capture an ultrasound image of the body region to be imaged in case of the ultrasound system being an ultrasound diagnostic imaging system in case it is determined, e.g. by the controller 140, that all ultrasound transducer cells 130 are properly acoustically coupled to the body region. Alternatively, the controller 140 may be controlled by the mobile communication device 300, in which case the mobile communication device 300 may provide a signal indicative of all ultrasound transducer cells 130 being properly acoustically coupled to the body region to the controller 140 through its communication unit 145, which signal may trigger the controller 140 to capture the image. The mobile communication device 300 may be adapted to automatically generate such a signal or may be adapted to generate such a signal in response to a user indicating that ultrasound transducer cells 130 are properly acoustically coupled to the body region, e.g. by the user providing the mobile communication device 300 with a command through any suitable type of user interface indicative of this fact.

In a particular advantageous embodiment, at least the ultrasound transducer array 100 of the ultrasound system is integrated in a garment such that the ultrasound transducer array 100 may be positioned onto a particular body region in a consistent manner such that ultrasound images may be generated with the ultrasound transducer array 100 in a consistent manner, thereby facilitating straightforward comparison of different ultrasound images acquired at different points in time, for example because the garment ensures that the ultrasound transducer array 100 is positioned against a body portion to be imaged (or treated with ultrasound radiation) in a consistent manner. For example, the garment may ensure that the body portion to be imaged or treated is deformed in a consistent manner upon application of the garment including the ultrasound transducer array 100 and that the ultrasound transducer array 100 is positioned against the body portion in a reproducible manner upon correct wearing of the garment by the patient. To this end, the garment may be designed to tightly or snugly fit the body portion of the patient.

Figure 8:
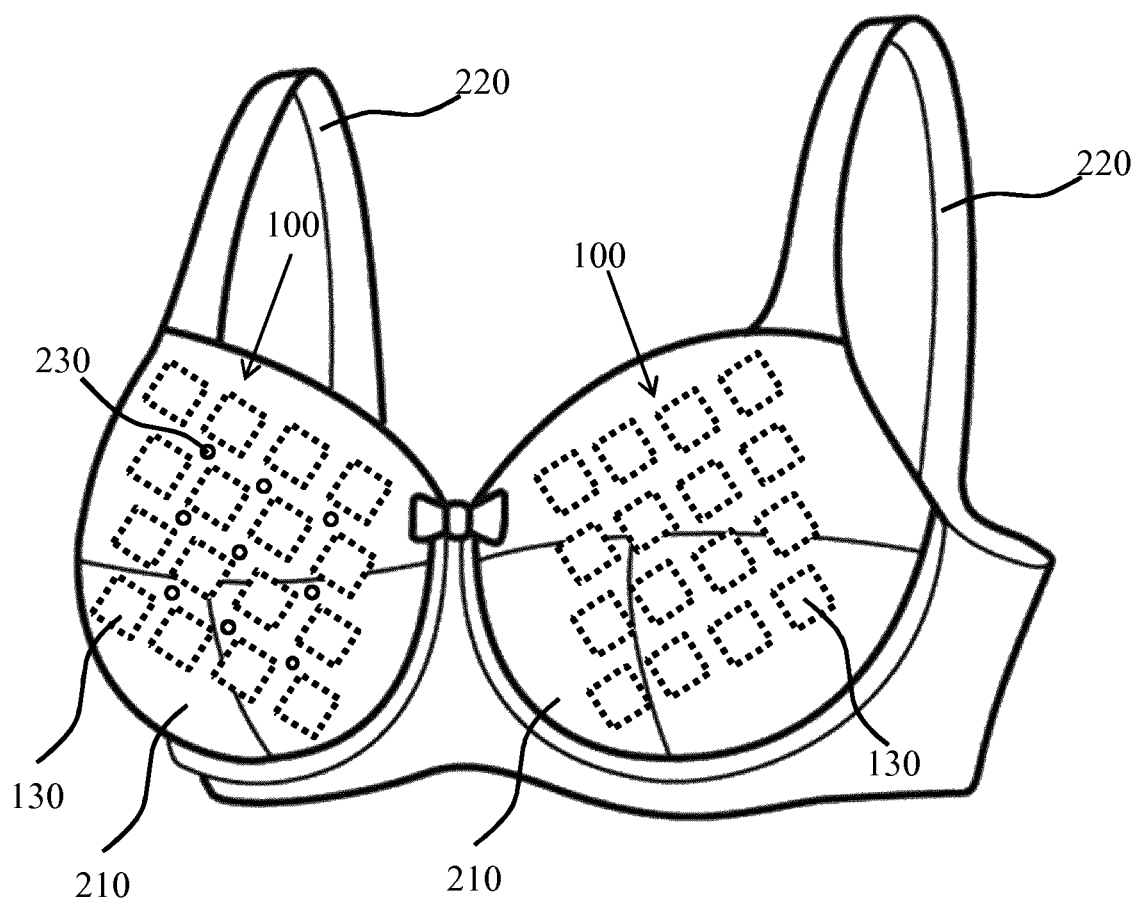
FIG. 8 schematically depicts an aspect of an ultrasound system according to a particularly advantageous embodiment.
Figure 9:
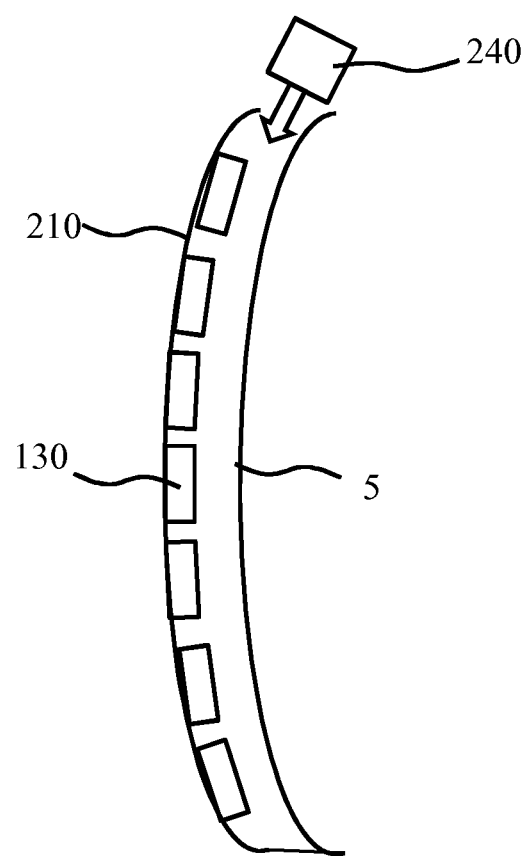
FIG. 9 schematically depicts an optional aspect of an ultrasound system of FIG. 8.

A particular example of such a garment is schematically depicted in FIG. 8, in which the garment is a brassiere 200 having cups 210, which cups may be dimensioned and shaped in accordance with specific breast sizes as is well-known per se. The brassiere 200 may further comprise straps 220, which straps may be adjustable to ensure that the brassiere 200 is kept in the correct position on the body of the wearer. Each cup 210 may comprise an independently controllable ultrasound transducer array 100 comprising a plurality of ultrasound transducer cells 130 having independently adjustable orientations such as to conform an ultrasound transmitting surface of each ultrasound transducer cell 130 to a region of a body, i.e. to a portion of the breast to be held in position by the cup 210. The ultrasound transducer array 100 may be mounted on an inner surface of the cup 210 to facilitate direct contact between the ultrasound transducer array 100 and the breast of the wearer of the brassiere 200.

Each ultrasound transducer array 100 may be controlled by the controller 140; alternatively, the ultrasound system may comprise dedicated controllers 140 for each of the ultrasound transducer arrays 100. Each ultrasound transducer array 100 may be implemented in any suitable fashion; for example, a flexible ultrasound transducer array 100 as described in more detail above may be integrated in each of the cups 210 of the brassiere 200. Alternatively, each ultrasound transducer cell 130 may be individually attached to such a cup 210. Other suitable arrangements of securing an ultrasound transducer array 100 within such a cup 210 will be immediately apparent to the skilled person. It should further be understood that alternative embodiments of a brassiere 200 in which only one of the cups 210 comprises such an ultrasound transducer array 100 are equally feasible.

Each cup 210 comprising an ultrasound transducer array 100 may further comprise a plurality of apertures 230 for receiving biopsy needles. Such biopsy needles may be visualized or imaged with the ultrasound transducer array 100 in the cup as the needles penetrate the skin of the breast in the cup 210, such that the biopsy needles may be guided to the appropriate tissue region within the breast with the aid of the ultrasound images generated with the ultrasound transducer array 100. Such apertures 230 may have any suitable shape, e.g. holes or tubes extending through the cup 210.

The cups 210 may be flexible cups or may be rigid cups, e.g. metal or plastic cups in which the ultrasound transducer array 100 is mounted on a flexible (malleable) material such as a foam or the like in order to ensure compliance, i.e. good acoustic coupling, of the respective ultrasound transducer cells 130 of the ultrasound transducer array 100 with the breast in such a cup 210. The quality of the acoustic coupling between the respective ultrasound transducer cells 130 and the breast may be determined as previously described in more detail with the aid of FIG. 6 and FIG. 7.

In order to further improve the acoustic coupling between the respective ultrasound transducer cells 130 and the breast of the wearer of the brassiere 200, the brassiere 200 may further include a dispensing unit 240 for dispensing an acoustic coupling gel between the ultrasound transducer cells 130 on the inner surface of the cup 210 and a portion 5 of the breast of the wearer of the brassiere 200. It should be understood that the spacing between the ultrasound transducer cells 130 and the portion 5 of the breast of the wearer of the brassiere 200 has been exaggerated to more clearly demonstrate where the acoustic coupling gel is applied, as indicated by the block arrow extending from the dispensing unit 240. Any suitable acoustic coupling gel may be used in the dispensing unit 240. The dispensing unit 240 may be manually operated by the wearer of the brassiere 200, e.g. by squeezing or otherwise releasing the acoustic coupling gel from the dispensing unit 240 or alternatively the dispensing unit 240 may comprise an actuated release mechanism responsive to the controller 140 such that the controller 140 may control the release of the acoustic coupling gel into the space between the ultrasound transducer cells 130 and the portion 5 of the breast upon detecting unsatisfactory acoustic coupling between the ultrasound transducer cells 130 and the breast as previously explained in more detail with the aid of FIG. 6.

A particular advantage of the incorporation of an ultrasound transducer array 100 in one or more cups 210 of the brassiere 200 is that a (3-D) image of the whole breast may be acquired rather than having to stitch separate images together as for instance is the case with hand-held ultrasound transducer probes, where the stitching of such separate images can be challenging due to the variation in pressure applied with the ultrasound probe to different regions of the breast as previously explained. Moreover, the integration of such an ultrasound transducer array 100 in a brassiere 200 facilitates examination or treatment of the patient in a number of positions, e.g. upright, supine or prone positions, without this having a material effect on the shape of the breast to be imaged or treated. It should furthermore be appreciated that such ultrasound examination is significantly safer compared to in particular x-ray screening due to the lack of use of ionizing radiation, which also allows younger and pregnant women to be screened in this manner.

The provision of a garment such as a brassiere 200 with ultrasound imaging capability further provides new opportunities for (female) patient screening. For example, the brassiere 200 may be sold to professional non-expert users such as general practitioners or nurses who themselves may not have the skills to acquire and read sonographic data. Instead, the acquired sonographic data, e.g. ultrasound images, may be transmitted, e.g. using the wireless communication unit 145, to a remote location offering a sonographic data interpretation service, which service for example may be provided using sonographic experts, e.g. in a hospital, a specialist clinic or the like. Alternatively, such a service may be an automated service in which the sonographic data is automatically interpreted using state-of-the-art image processing algorithms. Similarly, the garment may be sold to end-users, may use it for self-screening by providing the acquired sonographic data to a remote service as previously explained. Such a service may be provided as a paid service, for instance on a pay-per-use basis, or on the basis of the periodic subscription fee, e.g. a monthly or annual fee.

The controller 140 may be integrated in the garment, e.g. brassiere 200, or alternatively may be a portable or wearable unit distinct from the garment. For example, the controller 140 may be a portable unit that can be clipped onto a belt, carried in a handbag or the like or worn on the body in case of an ambulant ultrasound system. Alternatively, the controller 140 may be a user console or the like, to which the ultrasound transducer array 100 in the garment may be connected in any suitable manner, e.g. using a probe cable or the like. This for example is particularly suitable in case of a stationary examination or treatment unit, e.g. in a clinic or the like.

Figure 10:
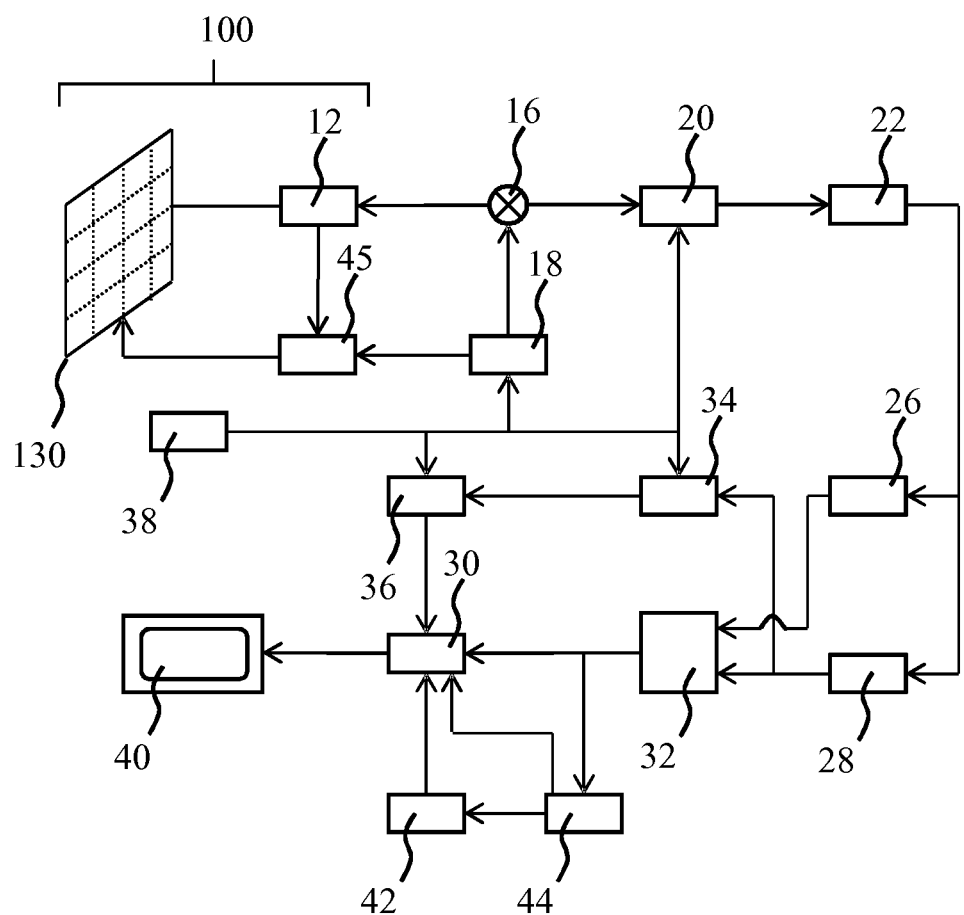
FIG. 10 schematically depicts a block diagram of an example embodiment of an ultrasound system.

FIG. 10 schematically depicts an example embodiment of an ultrasound imaging system 10 in which the controller 140 is provided as a user console to which the ultrasound transducer array 100 is communicatively coupled, e.g. using appropriate or the like as previously explained. It should however be understood that at least parts of the ultrasound imaging system 10 may be distributed, e.g. provided as a remote service, in particular those elements for which the skilled person will understand that these elements are deployed for the processing of the sonographic data captured with the ultrasound transducer array 100. In particular, FIG. 10 schematically depicts a block diagram of an example embodiment of the electronics that may be deployed to interface with and control the ultrasound transducer array 100 for the generation of ultrasound waves, e.g. ultrasound pulses, and reception of ultrasound echoes, e.g. pulse echoes, e.g. for diagnostic imaging purposes. The ultrasound transducer array 100 may be coupled to a microbeam former 12, which may be located in the ultrasound transducer array 100 in some embodiments, which controls transmission and reception of signals by the ultrasound transducer cells 130. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.) The microbeam former 12 may be coupled by a probe cable, e.g. coaxial wire, to a terminal, e.g. a user console device or the like including the controller 140, comprising a transmit/receive (T/R) switch 16 which switches between transmission and reception modes and protects the main beam former 20 from high energy transmit signals when a microbeam former 12 is not present or used and the transducer array is operated directly by the main system beam former 20. The transmission of ultrasonic beams from the ultrasound transducer array 100 under control of the microbeam former 12 may be directed by a transducer controller 18 coupled to the microbeam former 12 by the T/R switch 16 and the main system beam former 20, which receives input from the user's operation of the user interface through control panel 38. One of the functions controlled by the transducer controller 18 is the direction in which beams are steered and focused. Beams may be steered straight ahead from (orthogonal to) the transducer array, or at different angles for a wider field of view. The transducer controller 18 may be coupled to control the voltage source 45 for the ultrasound transducer array 100. For instance, the voltage source 45 sets the DC and AC bias voltage(s) that are applied to CMUT elements of a CMUT array, e.g. to operate the CMUT elements in collapse mode, as is well-known per se. The transducer controller 18 may be further adapted to control the voltage source 45 such as to switch the ultrasound transducer cells 130 to a low-power mode, e.g. in response to a temperature sensor signal indicative of the ultrasound transducer cells 130 reaching a critical temperature.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer cells 130 and/or from the individual ultrasound transducer elements of such ultrasound transducer cells 130. In this way the signals received by thousands of transducer elements of an ultrasound transducer array 100 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. Such a signal processor 22 may form part of the controller 140 or alternatively may form part of a remote system to which the beam-formed signals are communicated with the controller 140. The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information. As will be explained in more detail below, the signal processor 22 may further be adapted to register the individual images produced with the separate ultrasound transducer cells 130 of the ultrasound transducer array 100.

The processed signals may be forwarded to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40, which may be part of the controller 140 or may be part of a remote system in communication with the controller 140 as explained in more detail above. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the control panel 38, such as patient name.

The user interface may be coupled to the transducer controller 18 to control the generation of ultrasound signals from the ultrasound transducer array 100 and hence the images produced by the ultrasound transducer array 100 and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system 10 is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound transducer array 100 may not have 3D imaging capabilities and so on. Other variations will be apparent to the skilled person. Moreover, it should be understood by the skilled person that the aforementioned electronics may be adapted in case of the ultrasound system being an ultrasound therapy system. In particular, in case of such an ultrasound therapy system, the aforementioned electronic components associated with the ultrasound image forming and processing may be omitted from the ultrasound system as will be immediately apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:
1. An ultrasound system comprising:
an ultrasound transducer array comprising a plurality of ultrasound transducer cells, and a flexible mounting region defining a plurality of receiving portions, wherein the plurality of ultrasound transducer cells are mounted to a plurality of support members, wherein the plurality of support members onto which the ultrasound transducer cells are mounted are insertable into the plurality of receiving portions, respectively, enabling each ultrasound transducer cell of the plurality of ultrasound transducer cells to have an independently adjustable position and/or orientation such as to conform an ultrasound transmitting surface of the respective ultrasound transducer cell to a region of a body, wherein each support member comprises a mounting portion, to which one of the plurality of ultrasound transducer cells is mounted, and a pillar integrated with and extending from the mounting portion for insertion into one of the plurality of receiving portions; and a controller configured to:
  select a first ultrasound transducer cell of the plurality of ultrasound transducer cells, and generate a first ultrasound signal with the first ultrasound transducer cell;
  select a second ultrasound transducer cell of the plurality of ultrasound transducer cells, and generate a second ultrasound signal with the second ultrasound transducer cell simultaneously with generating the first ultrasound signal, the second ultrasound signal being distinguishable from the first ultrasound signal;
  operate remaining ultrasound transducer cells of the plurality of ultrasound transducer cells in a reception mode;
  receive respective first indications of reception of the first ultrasound signal from first receiving ultrasound transducer cells of the remaining ultrasound transducer cells, and receive respective second indications of reception of the second ultrasound signal from second receiving ultrasound transducer cells of the remaining ultrasound transducer cells;
  derive, for each of the first receiving ultrasound transducer cells, time-of-flight information of the first ultrasound signal from the first ultrasound transducer cell to each of the first receiving ultrasound transducer cells from the respective first indications;
  derive, for each of the second receiving ultrasound transducer cells, time-of-flight information of the second ultrasound signal from the second ultrasound transducer cell to each of the second receiving ultrasound transducer cells from the respective second indications; and
  determine relative positions and/or relative orientations of the plurality of ultrasound transducer cells based at least in part on the time-of-flight information of the first ultrasound signal and the time-of-flight information of the second ultrasound signal.

2. The ultrasound system of claim 1, wherein the first ultrasound signal and the second ultrasound signal have different frequencies.

3. The ultrasound system of claim 2, wherein the controller is configured to determine times of arrival of the first ultrasound signal at the first receiving ultrasound transducer cells and times of arrival of the second ultrasound signal at the second receiving ultrasound transducer cells from a power spectrum of the first ultrasound signal and the second ultrasound signal received by the first receiving ultrasound transducer cells and the second receiving ultrasound transducer cells, respectively.

4. The ultrasound system of claim 1, wherein the ultrasound system is at least one of a diagnostic imaging system or a therapy system.

5. The ultrasound system of claim 1, wherein the ultrasound transducer array is incorporated in a garment.

6. The ultrasound system of claim 5, wherein the garment is a brassiere comprising a pair of cups, at least one cup of the pair of cups comprising the ultrasound transducer array.

7. The ultrasound system of claim 6, wherein each cup of the pair of cups comprises an independently operable ultrasound transducer array.

8. The ultrasound system of claim 6, wherein each cup of the pair of cups further comprises a plurality of apertures for receiving biopsy needles.

9. The ultrasound system of claim 6, further comprising at least one dispenser for dispensing an acoustic coupling gel between the ultrasound transducer array in the at least one cup of the pair of cups and a breast of a patient.

10. The ultrasound system of claim 1, further comprising a transmission unit.

11. The ultrasound system of claim 10, wherein the controller is further configured to, for each ultrasound transducer cell of the plurality of ultrasound transducer cells:
  generate a further ultrasound signal with an ultrasound transducer cell of the plurality of ultrasound transducer cells;
  receive an echo signal of the further ultrasound signal from the ultrasound transducer cell;
  derive an acoustic coupling quality indication for the ultrasound transducer cell from a difference between the further ultrasound signal and the received echo signal; and
  transmit the acoustic coupling quality indication to a remote device with the transmission unit.

12. The ultrasound system of claim 1, wherein the flexible mounting region defines a sealed space in between the flexible mounting region and the region of the body, wherein evacuation of air from the sealed space results downward force transferred through each pillar to the plurality of ultrasound transducer cells, enhancing conformal contact of the plurality of ultrasound transducer cells with the region of the body.

13. The ultrasound system of claim 1, wherein the plurality of mounting portions are interconnected by a plurality of interconnecting regions, forming a flexible mat.

14. The ultrasound system of claim 1, wherein the controller is configured to spatially register the plurality of ultrasound transducer cells using the time-of-flight information of the first ultrasound signal and the time-of-flight information of the second ultrasound signal.

15. A method of operating an ultrasound system comprising an ultrasound transducer array comprising a plurality of ultrasound transducer cells, the method comprising:
  providing a flexible mounting region for the ultrasound transducer array defining a plurality of receiving portions, wherein the plurality of ultrasound transducer cells are mounted to a plurality of support members;
  inserting the plurality of support members onto which the ultrasound transducer cells are mounted into the plurality of receiving portions, respectively, enabling each ultrasound transducer cell of the plurality of ultrasound transducer cells to have an independently adjustable position and/or orientation such as to conform an ultrasound transmitting surface of the respective ultrasound transducer cell to a region of a body, wherein each support member comprises a mounting portion, to which one of the plurality of ultrasound transducer cells is mounted, and a pillar integrated with and extending from the mounting portion for insertion into one of the plurality of receiving portions;
  selecting a first ultrasound transducer cell of the plurality of ultrasound transducer cells, and generating a first ultrasound signal with the first ultrasound transducer cell;
  selecting a second ultrasound transducer cell of the plurality of ultrasound transducer cells, and generating a second ultrasound signal with the second ultrasound transducer cell simultaneously with generating the first ultrasound signal, the second ultrasound signal being distinguishable from the first ultrasound signal;
  operating remaining ultrasound transducer cells of the plurality of ultrasound transducer cells in a reception mode;

receiving respective first indications of reception of at the first ultrasound signal from first receiving ultrasound transducer cells of the remaining ultrasound transducer cells;

receiving respective second indications of reception of the second ultrasound signal from second receiving ultrasound transducer cells of the remaining ultrasound transducer cells;

deriving, for each of the first receiving ultrasound transducer cells, time-of-flight information of the first ultrasound signal from the first ultrasound transducer cell to each of the first receiving ultrasound transducer cells from the respective first indications;

deriving, for each of the second receiving ultrasound transducer cells, time-of-flight information of the second ultrasound signal from the second ultrasound transducer cell to each of the second receiving ultrasound transducer cells from the respective second indications; and determining relative positions and/or relative orientations of the plurality of ultrasound transducer cells based at least in part on the time-of-flight information of the first ultrasound signal and the time-of-flight information of the second ultrasound signal.

16. The method of claim 15, further comprising:

generating a further ultrasound signal with an ultrasound transducer cell of the plurality of ultrasound transducer cells;

receiving an echo signal of the further ultrasound signal from the ultrasound transducer cell;

deriving an acoustic coupling quality indication for the ultrasound transducer cell from a difference between the further ultrasound signal and the received echo signal; and wirelessly transmitting the acoustic coupling quality indication to a remote device.

17. The method of claim 16, further comprising:

displaying the acoustic coupling quality indication on a display of the remote device.

18. The method of claim 15, wherein the first ultrasound signal and the second ultrasound signal have different frequencies.

19. An ultrasound system comprising:

an ultrasound transducer array comprising a plurality of ultrasound transducer cells, and a flexible mounting region defining a plurality of receiving portions, wherein the plurality of ultrasound transducer cells are mounted to a plurality of support members, wherein the plurality of support members onto which the ultrasound transducer cells are mounted are insertable into the plurality of receiving portions, respectively, enabling each ultrasound transducer cell of the plurality of ultrasound transducer cells to have an independently adjustable position and/or orientation such as to conform an ultrasound transmitting surface of the respective ultrasound transducer cell to a region of a body, wherein each support member comprises a mounting portion, to which one of the plurality of ultrasound transducer cells is mounted, and a pillar integrated with and extending from mounting portion for insertion into one of the plurality of receiving portions; and a controller configured to:

select a plurality of transmitting ultrasound transducer cells of the plurality of ultrasound transducer cells, and simultaneously generate distinguishable ultrasound signals with the plurality of transmitting ultrasound transducer cells, respectively;

operate remaining ultrasound transducer cells of the plurality of ultrasound transducer cells in a reception mode to receive the ultrasound signals;

receive respective indications of receiving the ultrasound signals from the remaining ultrasound transducer cells;

derive, for each of the remaining ultrasound transducer cells, time-of-flight information of the ultrasound signals from the plurality of transmitting ultrasound transducer cells to each of the remaining ultrasound transducer cells from the respective indications; and determine relative positions and/or relative orientations of the plurality of ultrasound transducer cells based at least in part on the time-of-flight information.

* * * * *